United States Patent
Yuan et al.

(10) Patent No.: US 7,873,147 B2
(45) Date of Patent: Jan. 18, 2011

(54) RADIOSTEREOMETRIC CALIBRATION CAGE

(75) Inventors: Xunhua Yuan, London (CA); Rongyi Cai, London (CA); David Holdsworth, London (CA); Cecil Rorabeck, London (CA); Robert Bourne, London (CA); Petar Seslija, London (CA)

(73) Assignee: The University of Western Ontario, London, Ontario (CA)

( * ) Notice: Subject to any disclaimer, the term of this patent is extended or adjusted under 35 U.S.C. 154(b) by 73 days.

(21) Appl. No.: 12/265,325

(22) Filed: Nov. 5, 2008

(65) Prior Publication Data

US 2009/0116621 A1 May 7, 2009

Related U.S. Application Data

(60) Provisional application No. 60/985,315, filed on Nov. 5, 2007.

(51) Int. Cl.
*G01D 18/00* (2006.01)
(52) U.S. Cl. .................. 378/164; 378/205; 378/207
(58) Field of Classification Search .................. 378/164, 378/163, 205, 207
See application file for complete search history.

(56) References Cited

U.S. PATENT DOCUMENTS

| | | | | | |
|---|---|---|---|---|---|
| 1,553,229 | A | * | 9/1925 | Fraser | 33/474 |
| 1,904,234 | A | * | 4/1933 | Hoskin et al. | 378/163 |
| 2,399,424 | A | * | 4/1946 | Bliss | 378/192 |
| 4,048,507 | A | * | 9/1977 | de Gaston | 378/162 |
| 4,563,768 | A | * | 1/1986 | Read et al. | 378/37 |
| 4,618,978 | A | * | 10/1986 | Cosman | 378/164 |
| 4,719,646 | A | * | 1/1988 | Saunders et al. | 378/179 |
| 5,142,559 | A | * | 8/1992 | Wielopolski et al. | 378/205 |
| 6,044,132 | A | * | 3/2000 | Navab | 378/163 |
| 6,327,337 | B1 | * | 12/2001 | Tsunemi | 378/98.8 |
| 6,381,302 | B1 | * | 4/2002 | Berestov | 378/41 |
| 6,491,702 | B2 | * | 12/2002 | Heilbrun et al. | 606/130 |
| 6,776,526 | B2 | * | 8/2004 | Zeiss | 378/207 |
| 6,865,253 | B2 | * | 3/2005 | Blumhofer et al. | 378/65 |
| 7,186,023 | B2 | * | 3/2007 | Morita et al. | 378/207 |
| 7,241,045 | B2 | * | 7/2007 | Skalli et al. | 378/207 |
| 7,371,007 | B2 | * | 5/2008 | Nilsson | 378/207 |

OTHER PUBLICATIONS

Karrholm, J., 1989, Roentgen Stereophotogrammetry. Review of orthopedic applications. Acta Orthop Scand 60 (4), 491-503.

Karrholm, J., et al. Does early micromotion of femoral stem prostheses matter? 4-7-year stereoradiographic follow-up of 84 cemented prostheses. J. Bone Joint Surg Br 1994; 76(B). 912-7.

Karrholm, J. et al. 1997. Radiostereometry of Hip Prostheses: Review of Methodology and Clinical Results. Clinical Orthopaedics and Related Research (344), 94-110.

(Continued)

*Primary Examiner*—Edward J Glick
*Assistant Examiner*—Thomas R Artman
(74) *Attorney, Agent, or Firm*—Perry+Currier Inc.

(57) ABSTRACT

A calibration cage for use in Roentgen Stereophotogrammetric Analysis (RSA), comprising a biplanar configuration of two compartments, each with a fiducial plate at the bottom and a control plate at the top and parallel thereto, the fiducial and control plates of one compartment being oriented at approximately 90° to fiducial and control plates of the other compartment such that a region of interest is positioned on one side of the fiducial and control plates of both compartments.

20 Claims, 4 Drawing Sheets

OTHER PUBLICATIONS

Madanat, R. et al. 2005. Accuracy and precision of radiostereometric analysis in the measurement of three-dimentional micromotion in a fracture model of the distal radius. Journal of Orthopaedic Research 23 (2005) 481-488.

Makinen, T. J. et al. 2004. Precision measurement of the RSA method using a phantom model of hip prosthesis. Journal of Biomechanics 37 (2004) 487-493.

Makinen, T. J. et al. 2005. Comparison of digital and conventional radiostereometric image analysis in an ankle phantom model. Scandinavian Journal of Surgery 94: 233-238, 2005.

McCalden, Richard W. et al. 2005. Radiographic methods for the assessment of polyethylene wear after total hip arthroplasty. J. Bone Joint Surg. Am. 87(10), 2323-34.

Olsen, S. 1993. Noise Variance Estimation in Images. In the 8th Scandinavian Conference on Image analysis, Tromso, Norway.

Onsten, I. et al. 2001. Accuracy and precision of radiostereometric analysis in the measurement of THR femoral component translations: human and canine in vitro models. Journal of Orthopaedic Research 19 (2001) 1162-1167.

Rohrl, Stephan M. et al. 2004. Effect of Augmented cup Fixation on Stability, Wear, and Osteolysis: A 5-year follow-up of total hip arthoplasty with RSA. Jorunal of Arthoplasty vol. 19 (8), 962-71.

Ryd, Lief, 1986. Micromotion in knee arthoplasty. a roentgen stereophotogrammertric analysis of tibial component fixation. Acta Orthopaedica Scand Suppl 220. 1,3-80.

Ryd. Lief, et al. Methods for determining the accuracy of radiostereometric analysis (RSA). Acta Orthop Scand 2000; 71 (4), 403-8.

Selvik, G. 1989. Roentgen stereophotogrammetry. A method for the study of the kinematics of the skeletal system. Acta Orthop Scan Suppl 232. 1-51.

Selvik, G. 1990. Roentgen Stereophotogrammetric Analysis, Acta Radiologica 31 (2). 113-26.

Valstar, E. R. et al. 2000. Digital automated RSA compared to manually operated RSA compared to manually operated RSA. Journal of Biomechanics 33 (2000) 1593-1599.

Vrooman, Henri A. et al. 1998. Fast and accurate automated measurements in digitized sterophotogrammetric radiographs. Journal of Biomechanics 31 (1998)491-498.

Yuan, X, et al. 2000. Accuracy analysis for RSA: a computer simulation study on 3D marker reconstruction. Journal of Biomechanics 33 (2000) 493-498.

Yuan, X et al. 1997. Error propagation for relative motion determined from marker positions. Journal of Biomechanics 30 (9) 989-992.

Bragdon, Charles R. et al. 2002 Experimental assessment of precision and accuracy of radiostereometric analysis for the determination of polyethylene wear in a total hip replacement model. Journal of Orthopaedic Research 20 (2002) pp. 688-695.

Digas, Georgios et al. 2003. Highly cross-linked polyethylene in cemented THA—Clinical Orthopaedics and Related Research, No. 417, pp. 126-138.

Digas, Georgios et al. 2004. Highly cross-linked polyethylene in total hip arthroplasty—Clinical Orthopaedics and Related Research, No. 429—pp. 6-16.

Choo, Anthony M. T. et al. Improved RSA accuracy with DLT and balanced calibration marker distributions with an assessment of initial calibration—Journal of Biomechanics 36 (2003) 259-264.

Garling, Eric H. et al.—Marker Configuration Model-Based Roentgen Fluroscopic Ananysis—Journal of Biomechanics 38 (2005) pp. 893-901.

Digas, Georgios—(2005) New polymer materials in total hip arthroplasty, Acta Orthopaedica, 76: 1,4-82.

Borlin, Niclas et al.—RSA wear measurements with or without markers in total hip arthroplasty—Journal of Biomechanics 39 (2006) 1641-1650.

Allen, Matthew J. et al.—Technical feasibility and precision of radiosterometric analysis as an outcome measure in canine cemented total hip replacement. Journal of Orthopaedic Science (2004) 9:66-75.

Borlin, Niclas et al.—The precision of radiostereometric measurements. Manual vs. digital measurements—Journal of Biomechanics 35 (2002) 69-79.

Ioppolo, James et al.—Validation of a low-dose hybrid RSA and fluoroscopy technique: Determination of accuracy, bias and precision—Journal of Biomechanics 40 (2007) 686-692.

Dalen, Tore et al.—VersaBond bone cement—Prospective randomized study of the clinical properties of a new bone cement in total knee replacement . The Knee 12 (2005) 311-317.

H. J. Woltring et al. (1985) Finite Centroid and Helical Axis Estimation from Noisy Landmark Measurements in the Study of Human Joint Kinematics. Journal of Biomechanics, vol. 18, No. 5, pp. 379-389.

Inge Soderkvist et al. (1993) Determining the Movement of the Skeleton using Well-Configured Markers, Journal of Biomechanics, vol. 26, No. 12, pp. 1473-1477.

deBruin, PW, et al. Image-based RSA: Roentgen Stereophotogrammetric Analysis Based on 2D-3D Image Registration. J. Biomech. 2008; 41(1):155-64. Epub Aug. 15, 2007.

Habets, DF et al. Error Analysis of Marker-based Object Localization Using a Single-Plane XRII. J. Biomech. 2007, 40 (2):296-40, Epub Mar. 13, 2006.

Erickson, A et al. Fusion of Radiostereometric Analysis Data Into Computed Tomography Space: Application to the Joint Elbow. Invest Radiol. Oct. 31, 1996 (1):658:67.

Ellis, R et al. Use of a Biocompatible Fiducial Marker in Evaluating the Accuracy of Computed Tomography Image Restriction. J.Biomech Apr. 16, 2009; 42(6):686-691. Epub Mar. 3, 2009.

Tuijthof, GJ et al. Accuracy of a CT-based bone contour Registration Method to Measure Relative Bone Motions in the Hindfoot. Med Phys. Jan 27, 2000(1):30-8.

Fahrig, R. et al Three-Dimensional Computed Tomographic Reconstruction Using a C-arm Mounted XRII: Image-based Correction of Gantry Motion Nonidealities. Dept. of Medical Biophysics, Univ. of Western Ontario and the J.P. Robarts Research Institute, London, Canada.

* cited by examiner

RADIOSTEREOMETRIC CALIBRATION CAGE

CROSS REFERENCE TO RELATED APPLICATION

The present application claims the benefit of U.S. Provisional Patent Application No. 60/985,315, filed Nov. 5, 2007, the contents of which are incorporated herein by reference.

BACKGROUND OF THE INVENTION

1. Field of the Invention

The present invention is directed in general to medical imaging systems, and more particularly to a Roentgen Stereophotogrammetric Analysis (RSA) calibration cage and method of operation thereof.

2. Description of the Related Art

Computerized X-ray techniques are well known for investigating motion of the skeletal system, such as implant migration, fracture stability, joint kinematics, etc. In the field of arthroplastic surgery, stereophotogrammetry has been used to evaluate the stability of implanted prostheses following surgery. Specifically, Roentgen Stereophotogrammetric Analysis (RSA) has been shown to be a particularly accurate radiographic method for the analysis of implant motion and wear (Selvik, G., 1989: "Roentgen Stereophotogrammetry, A method for the study of the kinematics of the skeletal system, Acta Orthop Scand Suppl 232, 1-51).

RSA is based on the acquisition of two simultaneous radiographs from two different X-ray foci, in order to obtain a three-dimensional reconstruction of a relationship between prosthesis implant and bone or between two or more skeletal segments at one or more orientations in a range or motion of the joint between skeletal segments. Recognizable reference points or markers (e.g. tantalum beads) are located in respective regions of interest (e.g. a prosthesis and a bone, or between a pair of bones). Different RSA configurations are known in the art, each utilizing a different calibration cage for different clinical applications: a uniplanar setup for large joints, such as the hip and spine wherein the patient is positioned above a control plate and a pair of co-planar fiducial plates; and a biplanar setup, for small joints, such as the knee, elbow and ankle wherein the patient is positioned between the fiducial plate and the control plate.

The RSA calibration cage includes two arrays of markers for creating a three-dimensional coordinate system. The stereo images are used to determine the position of the markers of the regions of interest in relation to the three-dimensional coordinate system established by the calibration cage. The projection of fiducial markers and control points attached to the cage are used to establish the exposure geometry (i.e. the relationship between the X-ray foci, calibration cage, and the x-ray detector). Successive reconstructions are created at predetermined intervals following surgery, and software is used to evaluate and track micromotion of the implant or object of interest with respect to a reference point.

The fiducial and control markers are typically distributed relatively evenly across the fiducial and control plates (conventionally referred to as fiducial and control planes) so as to overlap within the field of projection of the object points. During examination using a prior art uniplanar RSA cage, the patient is placed above the cage with two X-ray beams crossing at an angle of about 40 degrees with each other. This examination is specifically designed for large joints such as the hip and spine. For small joints such as knees, elbows, etc. a biplanar cage is used. The examination object is placed inside the cage and two X-ray beams cross each other at a perpendicular orientation.

The overall accuracy and precision of the RSA technique depends on the performance of each element of the procedure, from synthetic landmark insertion, stereo radiographic examination, radiographic measurement, to the final data analysis. Many studies have been performed to improve the outcome of these RSA elements. However, whereas most previous studies have addressed methodologies for optimizing specific steps in the RSA clinical process, few investigations have focused on the importance of RSA calibration cage design in stereo radiographic examination. Although the calibration cage is understood to be a crucial factor in determining the performance of stereo examination, the quantitative relationship between cage design and the accuracy and precision of RSA remains largely unaddressed.

SUMMARY

According to one aspect of this specification, an RSA calibration cage is set forth configured as a biplanar setup with an open structure for use in imaging all manner of anatomic joints and all ranges of motion thereof. Consequently, the RSA cage set forth herein eliminates the prior art requirement to use different cages (uniplanar or biplanar) for imaging different skeletal joints.

According to another aspect, an optimal number of fiducial and control markers are positioned adjacent the edges of the fiducial and control plates in a rectangular pattern to prevent overlap with the object points, thereby improving RSA accuracy and precision during automated measurement. In such an embodiment the arrangement may include a single or plurality of control plates of parallel orientation to the fiducial plane.

These together with other aspects and advantages which will be subsequently apparent, reside in the details of construction and operation as more fully hereinafter described and claimed, reference being had to the accompanying drawings forming a part hereof, wherein like numerals refer to like parts throughout.

DETAILED DESCRIPTION OF THE PREFERRED EMBODIMENTS

Figure 1:
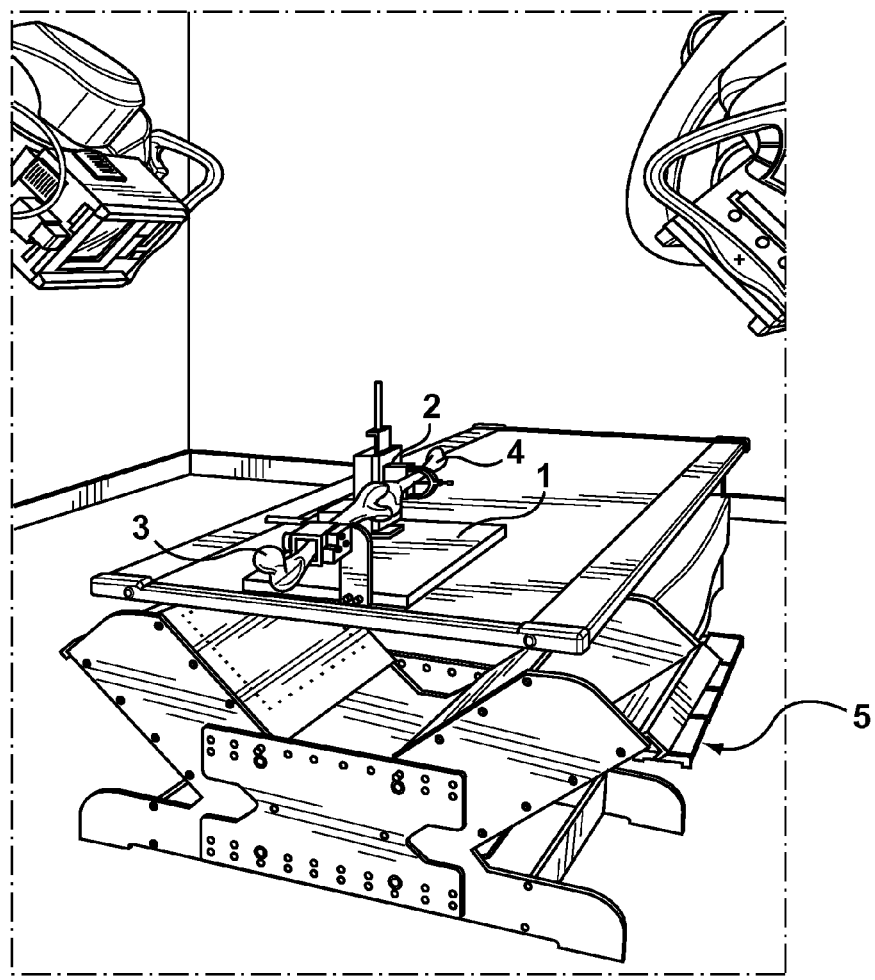
FIG. 1 shows a configuration of a biplanar RSA calibration cage with an open structure, according to an exemplary embodiment.
Figure 4:
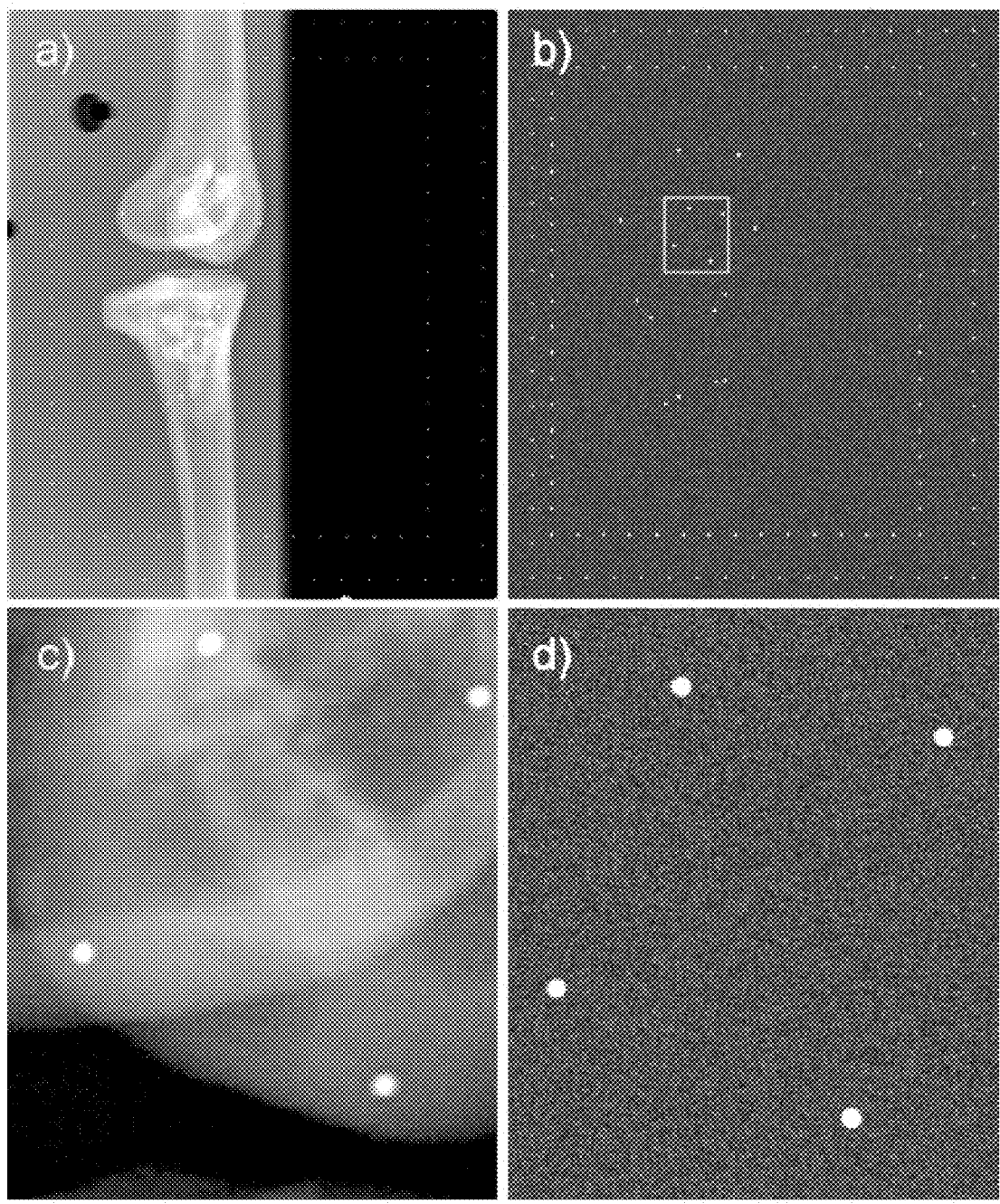
FIG. 4 shows a series of digital X-ray images, wherein a) shows the image from the phantom experiment according to the configuration of FIG. 1, b) shows a computer-synthetic image of the same configuration, c) is a magnified view of the region of interest identified in a), and d) is a magnified view of the region of interest identified in b).

With reference to FIG. 1, a knee joint phantom was constructed and used in experimental comparison among cage systems according to the prior art and the exemplary embodiment set forth in greater detail below with reference to FIG. 4. The phantom consisted of a polymethyl methacrylate (PMAA) base (1), a 3-D translation positioning stage (2), a solid foam femur (3) and a tibia (4). The femur (3) was fixed on the base (1) and the tibia (4) was rigidly attached to the positioning stage (2).

Figure 2:
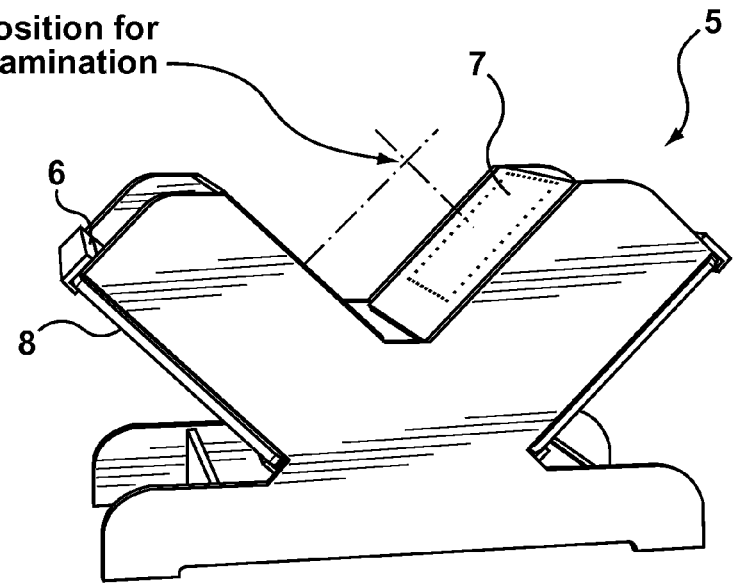
FIG. 2 is a perspective view of the exemplary RSA calibration cage of FIG. 1.

FIG. 2 illustrates details of the RSA cage (5) according to the exemplary embodiment of FIG. 1. Research has shown that a biplanar setup possesses higher accuracy and precision than a uniplanar configuration. Accordingly, the cage system of FIG. 2 is configured as a biplanar setup, but is provided with an open structure for accommodating a full range of object sizes and detection cassettes. Consequently, the cage (5) may be used for imaging of any anatomic joints having any ranges of motion.

The cage (5) comprises two compartments, each with a fiducial plate (6) at the bottom and a single control plate (7) or plurality of control plates at the top and parallel thereto. A detection cassette (8) or other appropriate x-ray detector is positioned adjacent and behind each of the fiducial plates (6). The detection cassette is one of a plurality of exemplary x-ray detection systems. However, the x-ray detector with which cage (5) is intended to be used is not limited to classical x-ray film-screen combinations but may include other types of detectors such as computed radiology cassettes (which employ a photostimulable phosphor to produce a latent image); radiography (DR) digital x-ray detectors using a flat-plate of either amorphous selenium or amorphous silicon; or direct radiography using an phosphor plate, optically coupled to a CCD, or such examples as would be obvious to one skilled in the art.

According to a prototype of the exemplary cage (5), the dimensions of each compartment were 460×380×208 mm. The angle of beam intersect between the dual x-ray sources (identified in FIG. 2 by the "optimal position for examination") is preferably approximately 90°. The incidence of the x-ray beam to the corresponding detection plane is preferably optimized at 90°. The fiducial and control plates (6 and 7) of one compartment are preferably oriented at an optimal angle of 90° to the fiducial and control plates (6 and 7) of the other compartment via a hinge point. As one skilled in the art may appreciate, the connection between the two planes at the hinge point may be a physical connection of the two planes or extrapolated from the two planes with no physical connection there between. Also, the optimal angle between the two planes is preferably 90° plus or minus 5°. In the event that it is not possible to attain the preferred 90° intersect of the two x-ray beams, one skilled in the art will appreciate that it is possible to maintain a 90° intersect of the beams toward the control and fiducial planes by altering the angle of the hinge point. Therefore, an improvement over the prior art is enjoyed by maintaining the open configuration, with optimal bead number and orientation, maintenance of parallel orientation of the single or plurality of control planes relative to the fiducial plane and utilization of an x-ray beam intersect between 40° and 85° with a corresponding hinge angle of between 40° and 85°, respectively.

Figure 3A:
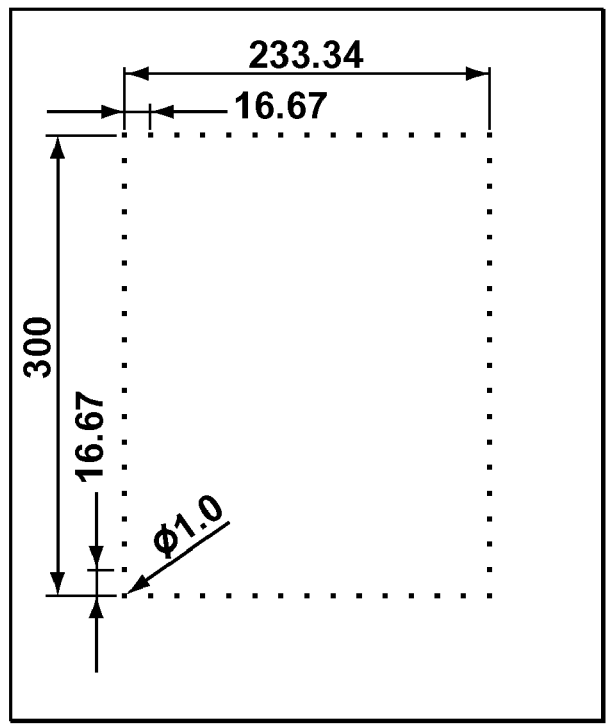
FIGS. 3A and 3B show bead marker configurations for control (FIG. 3A) and fiducial (FIG. 3B) plates, according to the exemplary embodiment.
Figure 3B:
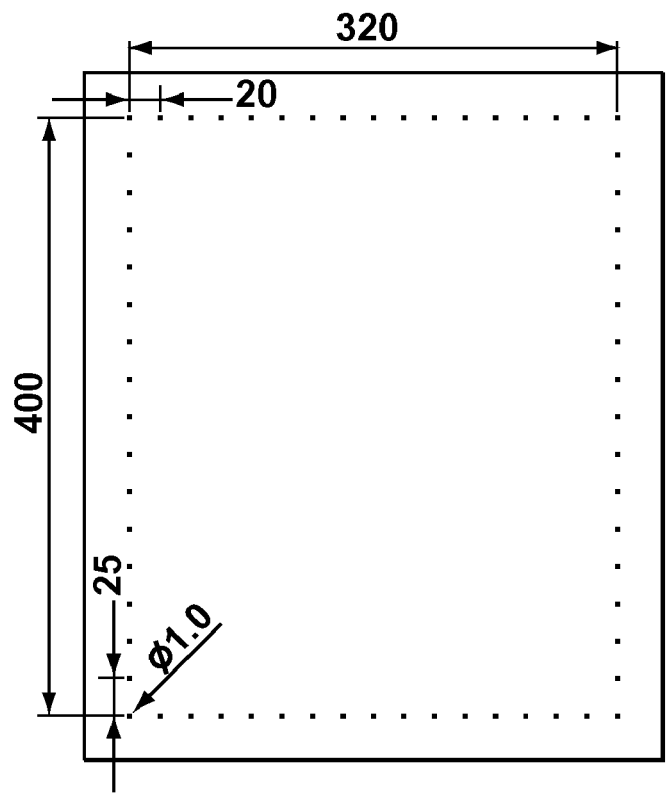

With respect to marker bead distribution, since fiducial marks and control points provide different functions, a different strategy than the conventional prior art was used with respect to the spacing and number of each. For fiducial marks, an equal number of beads were used on both long and short sides of the rectangular pattern, while control points were configured with equal spacing on all sides. Numerical simulations of bead number indicate that RSA precision is proportional to bead number. However, it was concluded that 64 fiducial marks and control points provide sufficient accuracy and precision in practice, with little gain expected beyond this number. Therefore in the embodiment set forth herein, 64 fiducial marks and 64 control points were utilized. More particularly, 64 spherical tantalum control points (Ø=1.0 mm) were positioned in a 300×233.34 mm rectangular pattern with marker spacing of 16.67 mm along both the long and short sides, as shown in FIG. 3A, and a corresponding 64 fiducial marks (Ø=1.0 mm) were set in a 400×320 mm rectangular pattern, with a marker spacing of 25 mm in the long side and 20 mm in the short side (FIG. 3B).

Figure 5A:
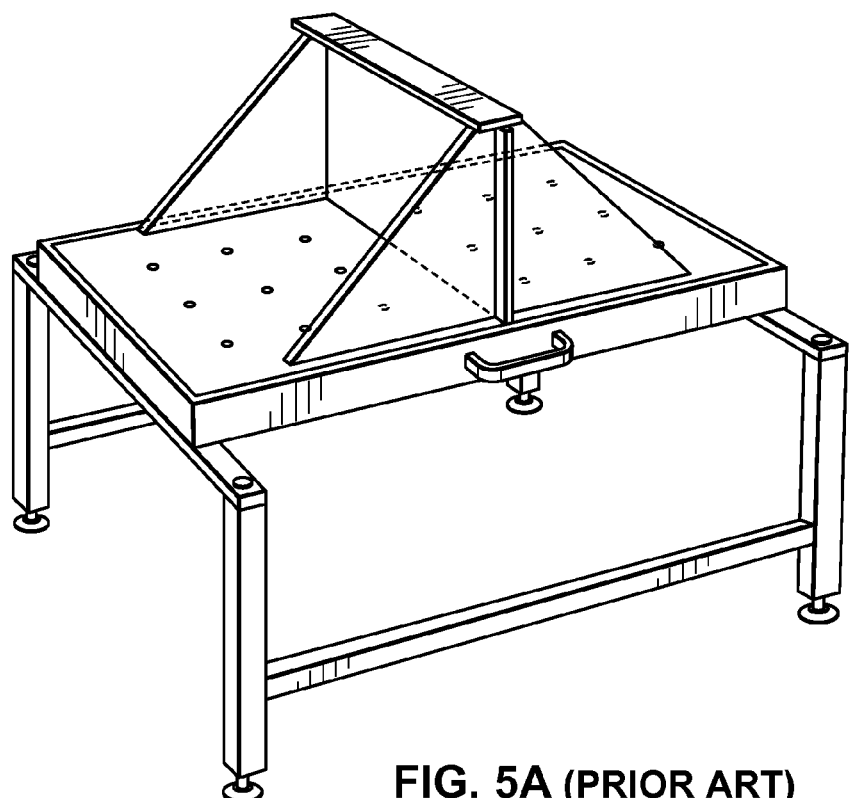
FIGS. 5A and 5B are perspective views of prior art uniplanar and biplanar RSA cages, respectively.
Figure 5B:
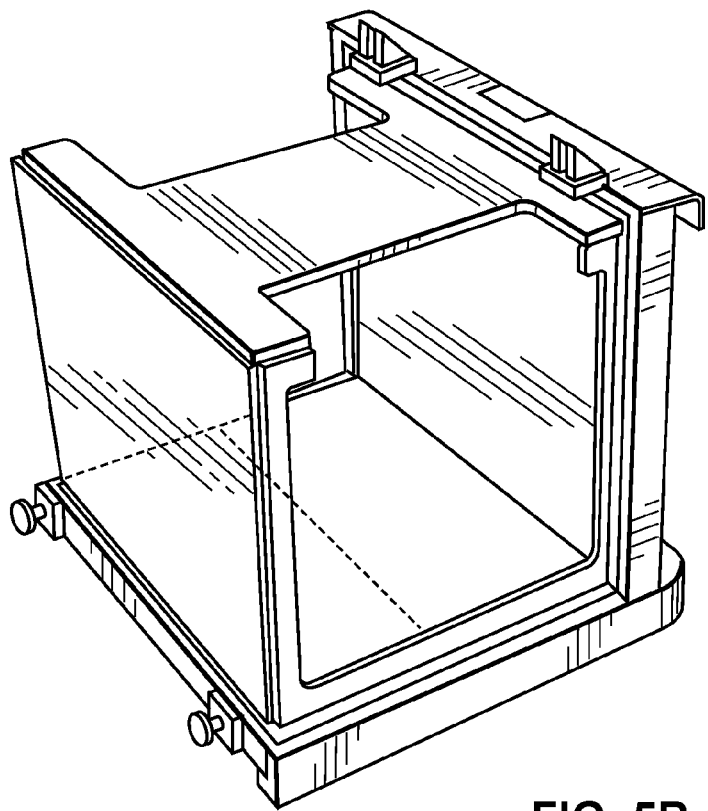

Experiments have been conducted in order to compare the performance of the exemplary RSA cage of FIG. 2 with prior art RSA cages. In FIG. 5A, a prior art uniplanar RSA cage is shown representing a dual plane system or dual x-ray source system with each detector plane arranged in a coplanar orientation relative to the other plane. In FIG. 5B, a prior art biplanar RSA cage is shown representing a dual plane system or dual x-ray source system wherein each detector plane is arranged in a non-coplanar orientation relative to the other plane.

According to one such experiment, eight tantalum beads (Ø=1.0 mm) were inserted into the distal femur and eight tantalum beads (Ø=1.0 mm) were inserted into the proximal tibia, according to the arrangement of FIG. 1. The midpoint between the femoral and tibial components was placed close to the optimal position of the RSA cage (5), wherein "optimal position" refers to the position where the two X-ray beams intersect, as shown in FIG. 2. The configuration of the two X-ray beams to each other at the optimal position is preferably at an angle of intersect of 90° plus or minus 5°. Other improved configurations of the detector planes, wherein the X-ray beam intersect angle at the optimal position is between 40° and 85°, may be achieved by altering the hinge angle between 40° and 85° to maintain the 90° incidence angle of the respective beams to the detector planes, as discussed above. Clinical RSA configurations were mimicked with an X-ray source-to-image distance (SID) of 140 cm and 40 degrees between the two X-ray beams for a prior art uniplanar cage, an example of which is illustrated in FIG. 5A; 100 cm SID and 90 degrees for a prior art biplanar cage, an example of which is illustrated in FIG. 5B; and 160 cm SID and 90 degrees for the exemplary RSA configuration illustrated in FIG. 2.

Two sets of phantom motion increments were applied in order to study accuracy and precision of the exemplary RSA cage set forth herein, respectively. For the precision investigation, zero motion was used between the femur (3) and tibia (4) and radiographic exposures were repeatedly taken twelve times. In order to characterize accuracy, sixteen random translation increments were performed along Y (proximal-distal), X (medial-lateral), and Z (anterior-posterior) axes, respectively. The increments applied were pre-calculated, based on a uniform distribution over the range of 0.02-1.73 mm to mimic clinical procedures.

The exposure parameters were selected as 70 kVp at 16 mAs for both the exemplary cage of FIGS. 1 and 2 and for the prior art uniplanar cage (FIG. 5A), and 50 kVp at 4 mAs for the prior art biplanar cage (FIG. 5B). Radiographic examinations were performed in a dedicated RSA lab with two ceiling-mounted X-ray units, as shown in FIG. 1, and digital images were acquired by a computed radiography digital X-ray system, which provided a 3520×4280 image matrix for a 35×43 cm cassette and 2364×2964 matrix for a 24×30 cm cassette. Resulting digital images were characterized by 0.1-mm pixel spacing and 10-bit gray scale level.

All images were measured by commercial RSA analysis software to determine marker locations. The two-dimensional measured marker locations were imported into a proprietary RSA computation program for the computation of 3-D marker reconstructions and motion calculations. The independent motion between femur (3) and tibia (4) was calculated from every two sequential image measurements. In total, six zero-motion situations and eight motion increments were investigated for each cage. The relative motion was characterized by six degrees-of-freedom, with three rotations and three translations. In the RSA calculation, all translation components were calculated in combination with the rotation components, with rotation components being less sensitive to error than translation components. Accordingly, only the translation components were evaluated. Independent motion between femur (3) and tibia (4) can be calculated over a range of motion from independent dual images obtained by RSA to provide an indication of dynamic changes in relative position of two or more points of interest across the series. Similarly, to one skilled in the art, the three dimensional structure of the object of interest may be obtained from dual plane RSA analysis, and subsequent range of motion and position evaluated using the information derived from either single x-ray source and images derived from the corresponding perpendicular plane.

Precision was evaluated along the X, Y, and Z axes, for the RSA cage of FIG. 2, and for the prior art uniplanar and biplanar designs of FIGS. 5A and 5B, respectively. Precision was calculated as the standard deviation of repeated simulations, under conditions of zero motion, with appropriate added random noise in marker localization. After fabrication of the exemplary RSA cage of FIG. 2, similar experimental analysis of precision was carried out with all three cage designs, to verify the validity of the numerical simulation and computer-synthetic image analyses.

Accuracy was also assessed from experimental measurements on all three cage designs, using linear-regression analysis to compare the measured motion with the true increments. Accuracy was presented as the 95% prediction interval (PI) as obtained by first determining the lower and upper bounds for the prediction interval for each observation and then calculating the mean of the intervals for each observation. Precision was calculated as described above. In order to address the statistical difference between cages, one-way analysis of variance (ANOVA) was then applied to the PI data sets for accuracy and the repeated measurements for precision, with P values of <0.01 deemed significant.

Both numerical simulation and computer-synthetic image analysis predicted improved precision, as shown in Table 1, below, which was verified by experimental comparison of accuracy and precision, as shown in Table 2, below, where the exemplary cage of FIG. 2 is identified as "new cage".

TABLE 1

|  |  | X ($\mu$m) | Y ($\mu$m) | Z ($\mu$m) |
|---|---|---|---|---|
| Numerical Simulation (N = 500) | New Cage | 5.0 | 3.6 | 5.2 |
|  | Biplanar Cage | 11.1 | 5.1 | 10.7 |
|  | Uniplanar Cage | 10.4 | 7.6 | 17.9 |
| Synthetic Image (N = 6) | New Cage | 4.1 | 2.6 | 4.3 |
|  | Biplanar Cage | 12.7 | 5.9 | 3.5 |
|  | Uniplanar Cage | 13.6 | 6.7 | 15.7 |
| Phantom Test (N = 6) | New Cage | 4.3 | 6.1 | 4.3 |
|  | Biplanar Cage | 10.4 | 9.4 | 12.0 |
|  | Uniplanar Cage | 13.9 | 6.1 | 18.0 |

TABLE 2

|  | Accuracy (95% prediction interval in $\mu$m) | Precision (SD of zero motion in $\mu$m) |
|---|---|---|
| New Cage | ±11 | 8 |
| Biplanar Cage | ±20 | 14 |
| Uniplanar Cage | ±39 | 28 |

Table 1 shows similar precision in all three directions for the "new cage", while prior art cages exhibit reduced precision in the X and Z directions, which involve out-of-plane localization. Also included in Table 1 are values of precision determined by experimental measurements using the phantom experimental setup of FIG. 1. It will be noted that the experimentally determined precision is generally in good agreement with simulation, thereby confirming the validity of the numerical simulation and computer-synthetic analyses.

The results shown in Table 2 indicate that the accuracy and precision of the "new cage" enjoyed an improvement of about 40% with respect to the biplanar cage (FIG. 5B) and 70% with respect to the uniplanar cage (FIG. 5A). Accuracy, defined by the 95% PI, was ±11 $\mu$m, ±20 $\mu$m and ±39 $\mu$m ($R^2$>0.99, P<0.01 for each linear regression equation) for the exemplary cage of FIG. 2, the biplanar cage of FIG. 5B, and the uniplanar cage of FIG. 5A, respectively. Precision, defined by the standard deviation in the case of zero-motion, was 8 $\mu$m, 14 $\mu$m and 28 $\mu$m for the exemplary cage of FIG. 2, the biplanar cage of FIG. 5B, and the uniplanar cage of FIG. 5A, respectively. The one-way ANOVA (Analysis of Variables) test indicated that the improvements of both accuracy and precision were significant (P<0.01).

In summary, the calibration cage of FIG. 2 represents a significant improvement in accuracy and precision of RSA, as compared to prior art designs. Optimization of the number of marker beads, the bead placement, and the configuration of the imaging planes as an optimization of the x-ray intersect angles and beam incidence to the x-ray detector as manipulated by variation of the dual plane intersect angle all contributed to the observed improvement, which was confirmed by two types of simulation and by experimental measurements with a phantom.

Accuracy and precision reported herein represents performance under idealized radiographic conditions (i.e. 50-70 kVp and reduced scatter without soft tissue). In practice, it is possible that accuracy and precision might not reach the levels indicated in Table 2. Nonetheless, the relative performance of different cage designs is believed to be reliably indicated in the results set forth herein. In particular, it is expected that the exemplary cage design of FIG. 2 will perform in clinical applications with approximately twice the reported precision and accuracy of existing prior art clinical cages. It is expected that the accuracy and precision of the optimized RSA system using the cage of FIG. 2 will approach ±55 $\mu$m in clinical implementation. In addition, the system has the versatility to accommodate any range of joint or skeletal element due to the open plane design.

The many features and advantages of the invention are apparent from the detailed specification and, thus, it is intended by the appended claims to cover all such features and advantages of the invention that fall within the true spirit and scope of the invention. For example, although a successful prototype has been described wherein the dimensions of each compartment were 460×380×208 mm, a person of skill in the art will appreciate that the dimensions are scalable while preferably preserving the optimal approximately 90° angle between the intersecting x-ray beams, the incidence of the beams to their respective parallel control and fiducial control plates, and the hinge angle between the respective compartments, and the optimal approximately 64 fiducial marks and control points. Also, a person of skill in the art will appreciate that the embodiments set forth herein may be modified to adopt to variations in cassette (i.e. computed radiography, direct digital radiography, classical x-ray film, etc.) variations in the intersect of dual parallel planes at the hinge versus a literal intersect (i.e. separation by space), to accommodate specific hardware setups, etc. Moreover, a person of skill in the art will understand that the tantalum bead size need not be restricted to Ø=1.0 mm, but rather a range of bead sizes is available.

Since numerous modifications and changes will readily occur to those skilled in the art, it is not desired to limit the invention to the exact construction and operation illustrated and described, and accordingly all suitable modifications and equivalents may be resorted to, falling within the scope of the invention.

The invention claimed is:

1. A calibration cage for use in Roentgen Stereophotogrammetric Analysis (RSA), comprising a biplanar configuration of first and second compartments, each with a fiducial plane and at least one control plane parallel to said fiducial plane, said fiducial and control planes of said first compartment being oriented at a predetermined angle of less than 180° to the fiducial and control planes of the second compartment thereby establishing a region of interest positioned on the same side of both the fiducial and control planes of both said first and second compartments.

2. The calibration cage of claim 1, wherein each said fiducial plane is disposed at a bottom portion of a respective one of said compartments, and each said control plane is disposed at a top portion of a respective one of said compartments.

3. The calibration cage of claim 1, wherein each said fiducial planes and control planes includes a plurality of fiducial and control markers positioned adjacent edges thereof in a rectangular peripheral pattern.

4. The calibration cage of claim 3, wherein each of said control planes includes 64 control markers in a 300×233.34 mm rectangular pattern with a marker spacing of 16.67 mm.

5. The calibration cage of claim 4, wherein each of said fiducial markers has a diameter of Ø=1.0 mm.

6. The calibration cage of claim 3, wherein each of said fiducial planes includes 64 fiducial markers in a 400×320 mm rectangular pattern with a marker spacing of 25 mm across a long side of said rectangular pattern and 20 mm along a short side of said rectangular pattern.

7. The calibration cage of claim 6, wherein each of said fiducial markers has a diameter of Ø=1.0 mm.

8. The calibration cage of claim 1, wherein said fiducial and control planes of said first compartment are oriented relative to the fiducial and control planes of the second compartment via a hinge point.

9. The calibration cage of claim 8, wherein said hinge point includes a physical connection between said fiducial and control planes of said first compartment and the fiducial and control planes of the second compartment.

10. The calibration cage of claim 8, wherein said hinge point is at a point of extrapolation of said fiducial and control planes of said first compartment and the fiducial and control planes of the second compartment.

11. The calibration cage of claim 8, wherein said hinge point defines said predetermined angle between said fiducial and control planes of said first compartment and the fiducial and control planes of the second compartment to be 90° plus or minus 5°.

12. The calibration cage of claim 8, wherein said hinge point defines said predetermined angle between said fiducial and control planes of said first compartment and the fiducial and control planes of the second compartment to be in a range of 40° to 85°.

13. The calibration cage of claim 8, wherein said hinge point defines said predetermined angle between said fiducial and control planes of said first compartment and the fiducial and control planes of the second compartment to approximate an angle of beam intersect between a pair of x-ray beams directed toward said respective control and fiducial planes.

14. The calibration cage of claim 13, wherein said predetermined angle and said angle of beam intersect are each approximately 90° plus or minus 5° for preserving an approximate perpendicular incidence of each said pair of x-ray beams to said respective control and fiducial planes.

15. The calibration cage of claim 13, wherein said predetermined angle and said angle of beam intersect are each in a range of 40° to 85° for preserving an approximate perpendicular incidence of each said pair of x-ray beams to said respective control and fiducial planes.

16. Use of the calibration cage of claim 1 to provide a dynamic Roentgen Stereophotogrammetric Analysis (RSA) series of independent dual images showing independent motion between at least two points of interest over a range of motion.

17. Use of the calibration cage of claim 1 to provide a three dimensional structure of an object of interest from dual plane analysis, and subsequent range of motion and position evaluation using images from a single plane and source of radiation.

18. Use of the calibration cage of claim 1 to provide Roentgen Stereophotogrammetric Analysis (RSA) with a film-screen x-ray detector.

19. Use of the calibration cage of claim 1 to provide Roentgen Stereophotogrammetric Analysis (RSA) with a computed radiography system.

20. Use of the calibration cage of claim 1 to provide Roentgen Stereophotogrammetric Analysis (RSA) with a direct digital system.

* * * * *